(12) United States Patent
Tian et al.

(10) Patent No.: US 7,294,247 B1
(45) Date of Patent: Nov. 13, 2007

(54) ELECTROPHORETIC SEPARATING DEVICE AND METHOD FOR USING THE DEVICE

(75) Inventors: Zhao-Wu Tian, Fujian (CN); Hua-Shui Lin, Fujian (CN); Yong-Liang Zhou, Fujian (CN)

(73) Assignees: Xiamen University, Fujian (CN); Institute for Biomedical Engineering IBMT, Ingbert (DE)

( * ) Notice: Subject to any disclaimer, the term of this patent is extended or adjusted under 35 U.S.C. 154(b) by 98 days.

(21) Appl. No.: 10/415,083

(22) PCT Filed: Oct. 25, 2000

(86) PCT No.: PCT/EP00/10494

§ 371 (c)(1),
(2), (4) Date: Aug. 25, 2003

(87) PCT Pub. No.: WO02/35223

PCT Pub. Date: May 2, 2002

(51) Int. Cl.
*G01N 27/447* (2006.01)
*G01N 27/453* (2006.01)

(52) U.S. Cl. ............... 204/451; 204/455; 204/601; 204/605

(58) Field of Classification Search ........ 204/451–455, 204/601–605
See application file for complete search history.

(56) References Cited

U.S. PATENT DOCUMENTS

| | | | |
|---|---|---|---|
| 5,296,114 A | 3/1994 | Manz | |
| 5,599,432 A | 2/1997 | Manz et al. | |
| 6,159,353 A * | 12/2000 | West et al. | 204/601 |
| 6,326,083 B1 * | 12/2001 | Yang et al. | 428/429 |
| 6,375,817 B1 * | 4/2002 | Taylor et al. | 204/453 |
| 6,685,809 B1 * | 2/2004 | Jacobson et al. | 204/450 |

FOREIGN PATENT DOCUMENTS

| | | |
|---|---|---|
| DE | 4314755 A1 | 11/1994 |
| EP | 0376611 A2 | 7/1990 |
| EP | 0653631 A2 | 5/1995 |

OTHER PUBLICATIONS

*Capillary electrophoresis on microchip*, Vladislav Dolnik, Shaorong Liu, Stevan Jovanovich, Electrophoresis 2000, 21, 41-54, Wiley-Vett Verlag GmbH, 69451 Weinheim 2000.

* cited by examiner

*Primary Examiner*—Alex Noguerola
(74) *Attorney, Agent, or Firm*—Buchanan Ingersoll & Rooney PC

(57) ABSTRACT

The invention concerns to an electrophoretic separation device comprising a separation channel having at least one in- and outlet opening at the beginning and at the end of the channel and one electrode in the region of the inlet opening and one electrode in the region of the outlet opening. As well the invention concerns to a method for electrophoretic separation. The invention is characterized in that said separation channel is subdivided into at least two sections in series being coupled mutually by a joint providing an electrical connection means having a ion-conductive material separating said channel from a reservoir being apart the channel and provided with an electrode.

22 Claims, 4 Drawing Sheets

ELECTROPHORETIC SEPARATING DEVICE AND METHOD FOR USING THE DEVICE

FIELD OF THE INVENTION

This application is a national stage application under 35 U.S.C. §371 of International Application No. PCT/EP00/10494 filed on Oct. 25, 2000, the content of which is hereby incorporated in its entirety by reference.

The invention concerns an electrophoretic separation device comprising a separation channel having at least one in- and outlet opening at the beginning and at the end of the channel and one electrode in the region of the inlet opening and one electrode in the region of the outlet opening. Further the invention concerns to method for electrophoretic separation by using said device.

BACKGROUND OF THE INVENTION

Much of the progress of modern medicine, environmental protection and materials development and production can be assigned to the advances in chemical analytical systems that permit the separation, identification, characterization and quantification of various chemical moieties. Separating the components of a sample mixture is one of the key processes in an analytical procedure. Components so separated can be individually identified and quantified.

Electrophoresis separates chemical components of a sample on the basis of their component-specific migration rate in an applied electric field along a separation path. A large number of biological or chemical molecules/macromolecules are charged in aqueous solutions at appropriate pH values. For example proteins are amphoteric and their charge varies from positive to negative, depending on the protein and the pH-value. Electrophoretic separation methods are based on the different mobilities of the individual components of the sample in an electrophoresis medium when an electric field is applied. The electrophoretic mobility of each individual component is the velocity it attains for a given external electric field and corresponds to the ratio between charge of the component and its frictional drag. The sample is applied as a narrow zone in the separation path and electrophoretic migration is started by the application of the electric field. Each component migrates at its specific rate along the separation path and forms a so-called band. Each band can be characterized by a peak, where the component concentration is maximal, and a width, being the distance between points on either side of the peak where the concentration falls below a certain threshold value. The width of the sample zone produced by the application of the sample and subsequent diffusion contribute to the widths of the electrophoretic bands.

Generally the following performance criteria are important for electrophoretic separation methods.

Resolution. Two components are usually separated when their migration distances differ more than the sum of the half-widths of their electrophoretic bands.

Detection limit. The lower detection limit of a component in a given sample decreases with the width of its separated band. The narrower this band is, the higher the concentration of the separated compound in the band will be and the better its detection can be.

Speed and throughput. Throughput is proportional to the number of parallel separations, for example in an array of separation channels, and inversely proportional to the time for one separation.

Convenience, practicability and cost-effectiveness. Miniaturization of CE, for example in chip format, can provide the fulfilling of these criteria (REF). These criteria are important for point-of-care and point-of-use applications of CE.

Minimizing the bandwidth of the separated components essentially contributes to fulfil the criteria of high resolution and low detection limit. Two main factors contribute to the width of the electrophoretic band, the width of the applied sample zone and its broadening due to diffusion during electrophoresis. The volume of the applied sample solution which is required for the detection of the components of interest determines the width of the sample zone. The majority of practical samples, for example in medicine or environmental and bioprocess monitoring, are concentration-limited, i.e. samples where the amount of the component to be analyzed is limited by its concentration in the sample and not by the available sample volume.

Usually high-resolution and sensitive electrophoretic separations of concentration-limited samples require a (pre-)concentration step. One problem underlying this invention is the convenient realization of the concentration step in a miniaturized capillary electrophoresis device and method. Hitherto concentration steps were achieved by discontinuous electrophoretic media in the separation channel, e.g. in polyacrylamide disc electrophoresis where a sample is concentrated at the boundary between different gels and buffers (REF). Discontinuous electrophoretic media in capillary electrophoresis can only be realized by cumbersome and tedious techniques, and only once for each sample.

Capillary electrophoresis is a widely used, well established analytical separation technique in bioscience, in pharmaceutical, environmental, food and other chemical analyses. In capillary electrophoresis a sample is injected into a carrier medium, where the individual components migrate at different rates in an applied external electrical field along the separation path, with the result that the sample is separated into its components. The separated components usually are determined by a detector connected to the capillary separating path (e.g. optical detector for fluorescence detection). Conventional high performance capillary electrophoresis (HPCE) instruments apply fused silica capillaries of 25–75 μm inner diameter and up to 1 m length and apply voltages of 10–30 kV. Special surface modifications, such as coatings, are used to improve separation performance. A typical separation procedure takes about 5–30 minutes.

Microfabricated, miniaturized capillary electrophoresis chips were introduced in 1992, see A. Manz, D. J. Harrison, E. M. J. Verpoorte, J. C. Fettinger, A. Paulus, H. Ludi, H. M. Widmer, J. Chromatogr. 593 (1992) S. 253. Separations e.g. of fluorescent dyes (see D. J. Harrison, A. Manz, Z. Fan, H. Ludi, H. M. Widmer, Anal. Chem. 64 (1992) S.1926 and see also S. C. Jacobson, R. Hergenroeder, L. B. Koutny, R. J. Warmack, J. M. Ramsey, Anal. Chem. 66 (1994) S.1107), fluorescently labeled amino acids (see D. J. Harrison, K. Fluri, K. Seiler, Z. Fan, C. S. Effenhauser, A. Manz, Science 161 (1993) S.895; C. S. Effenhauser, A. Manz, H. M. Widmer, Anal. Chem. 65 (1993) S.2637; S. C. Jacobson, R. Hergenroeder, A. W. Moore, J. M. Ramsey, Anal. Chem. 66 (1994) S.4127) and metal ion complexes (S. C. Jacobson, A. W. Moore, J. M. Ramsey, Anal. Chem. 67 (1995) S.2059) have shown that the separation speed of such devices can be increased by about more than one order of magnitude.

Therefore miniaturized capillary electrophoresis chips have been used for rapid analysis of biological samples, e.g. DNA restriction fragments (A. T. Wooley, R. A. Mathies, Proc. Natl. Acad. Sci. USA 91(1994) S.11348; S. C. Jacobson, J. M. Ramsey, Anal. Chem. 68 (1996) S.720), DNA sequencing fragments (A. T. Wooley, R. A. Mathies, Anal. Chem. 67 (1995) S.3676), PCR products (see S. C. Jacobson, J. M. Ramsey, Anal. Chem. 68 (1996) S.720) and short oligonucleotides (C. S. Effenhauser, A. Paulus, A. Manz, H. M. Widmer, Anal. Chem. 66 (1994) S.2949).

Also miniaturization aims at the integration of electrophoretic separation into total-analysis-systems (µTAS) or lab-on-a-chip solutions.

Miniaturization of capillary electrophoresis promises besides aspects of high separation performance also economic aspects like cost-effective production as well as the possibility of operation by untrained personnel including highly reliable procedures.

An electrophoretic separating device as well an electrophoretic separating method is disclosed in U.S. Pat. No. 5,296,114. The device comprises a separating channel which is constructed basically in form of a closed loop for example in form of a square. At each corner of the square at least one opening is provided having an electrode. A sample to be separated is introduced via a feed opening into said separating channel which is filled with an electrolytic carrier medium. The dissolved sample is moved with the aid of an electrical field through the channel, which is provided by the electrodes in the regions of the openings and is separated into individual components by the electrical field. The electrical field is generated in the channel by connecting electrodes in the region of the openings to different potentials of a voltage source. Due to the fact that the separating channel is square no dense packing of a multitude of separating channels isn t possible to arrange onto one carrier substrate.

In summary, a miniaturized CE separation device which can conveniently achieve a narrow bandwidth of the separated components from a concentration-limited sample has not been disclosed yet and hence is the objective of the described invention.

SUMMARY OF THE INVENTION

It is an object of the invention to provide a device and a method for fast and convenient, high-performance and cost-effective electrophoretic separation of complex samples. Good separation performance shall be implemented by the realization of sample concentration in an electrophoretic channel filled with a homogeneous medium resulting in narrow electrophoretic bandwidths.

It is a further object of the invention to miniaturize the separating device onto chip-based systems. The use of the device as well the handling of the electrophoretic separating method shall be easy and secured.

The solution of the object is disclosed in claim 1 describing an electrophoretic separating device which is also applicable for analyzing purposes. Claim 15 comprises an electrophoretic separating method by using said inventive device. Features which improve the inventive idea of claim 1 and 15 are described in the dependant claims as well in the whole disclosure with reference to the embodiments shown in the drawings.

An inventive electrophoretic separation device comprising a separation channel having at least one in- and outlet opening at the beginning and at the end of the channel and one electrode in the region of the inlet opening and one electrode in the region of the outlet opening is characterized in that said separation channel is subdivided into at least two sections in series being coupled mutually by a joint providing an electrical connection means having a ion-conductive material separating said channel from a reservoir being apart the channel and provided with an electrode.

The problem of low electrophoretic separation performance of concentration-limited samples, especially in miniaturized CE, is overcome by the invention which can generate a discontinuous electric field along the separation channel which is filled with a homogeneous medium. The electrophoresis channel consists of several, at least two, sections (n≧2) in series with n−1 joints between n sections. To establish different electric fields in the consecutive sections, electrodes are connected at the joints. To avoid disturbances in the separation channel by electrochemical reaction products and gas-bubble formation, these electrode connections are realized by inserting a solid ion conductive material as a membrane between the electrophoresis channel and a vial apart the channel. These vials are provided with electrodes and filled with appropriate electrolyte. By connecting the vial-electrodes to a direct current voltage supply, the buffer ions in the electrolyte can be interchanged through the ion-conductive membrane between the vials and the separation channel. By selecting appropriate membrane, the passing of sample ions to be analyzed can be prohibited by selectivity of the membrane. Thus a purely ionic connection to the joints of the separation channel is realized.

The separation procedure is conducted in several steps. Starting separation of complex sample mixtures, the sample is injected into the first section and may occupy a long sample zone, whose length ideally may be comparable to the length of the complete first section, that means the distance from the inlet opening to the first joint. The second section follows along the channel after the first section and describes the path of the separating channel from the first joint to the outlet opening in case of having just two sections otherwise there will be more joints along the separating channel.

In the first step or period, different electric fields are set up in the first and second sections. All the components in the sample mixture migrate from the first section to the second section passing through the joint. Since the ratio of the electric field in the first section to the electric field in the second section is a number R1 greater than 1, the bandwidth of each component is compressed and thus concentrated by the same ratio R1. The separation of different components takes place according to their differences in electrophoretic mobility and, more specifically in the invented device, according to the different mobility of each species in the respective section. The first step or period is terminated when the whole sample zone has moved from the first section to the second section.

In the second period, all species are driven by electric field and move from the second section into a third section passing through a second joint. Since the ratio of the electric field in the second section to the electric field in the third section is a number R2 (generally less than R1) greater than 1, the zone length of each species is generally compressed and concentrated once again by the ratio R2 and further separation of different species takes place. The second period is finished when the whole sample zone has moved from the second section to the third section. It is pointed out, that the electric fields in each section can be varied from period to period and from section to section.

For the analysis of more complex system, further sections and periods can be arranged similar to the former periods to obtain better resolution and to lower the limit of detectable concentration, if necessary.

At the end of electrophoresis, electric fields are switched off, and an image of the separation pattern is immediately taken by for example a CCD-camera and processed by computer. Alternatively, time dependent monitoring of electrophoresis by optical recording at one or many points of the separation channel can be performed.

BRIEF DESCRIPTION OF THE DRAWINGS

The invention is described without limiting the general inventive idea with reference to embodiments shown in the following drawings.

DETAILED DESCRIPTION OF THE INVENTION

Figure 1:
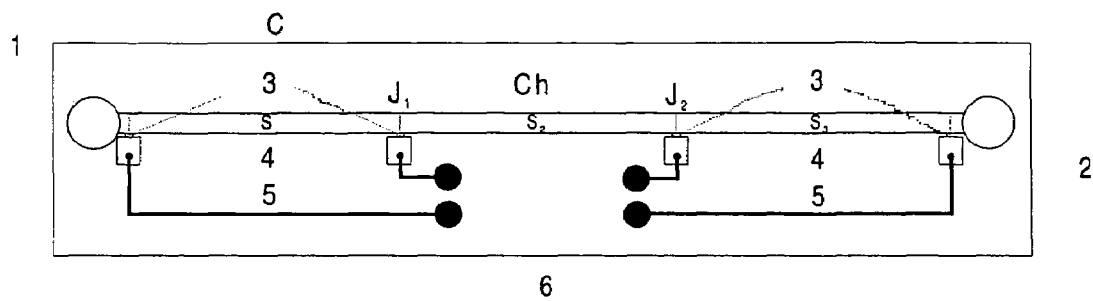
FIG. 1 Schematic sketch of an electrophoretic separating device.

FIG. 1 shows an electrophoretic separating device C having the electrophoresis channel Ch consists of several sections $S_n$ (e.g. n=3 or 4) in series with n−1 joints $J_{n-i}$ between n sections. The channel is made of one piece advantageously is provided with in- and outlet 1, 2 openings at the ends. A sample to be separated is injected via a feed opening (e.g. identical with the inlet (1)) into an electrophoretic carrier medium. In the channel sections different electric fields are generated by electrodes in the region of the in- and outlet openings and at the joints between the sections.

To prevent electrochemical reactions and gas-bubble formation in the separation channel Ch, the electric fields in the channel are established using ion-conductive materials 3, constructed for example as a membrane, between the channel Ch and a reservoir 4 apart the channel, provided with an electrode 5, which can be connected by interconnections 6 to direct voltage sources, and filled with appropriate electrolyte as source for ions, which are interchangeable with the buffer ions in the electrophoresis channel. The separation and compression of sample zones take place due to the different mobilities of each species in the consecutive sections, induced by different electric fields. The purpose of the invention is to establish a powerful electrophoresis method for high performance capillary electrophoresis HPCE, which combines the special merits of chip based systems (e.g. velocity, low operation voltage) with improved separation resolution, detection-limit and cost-effective fabrication.

For realization of an electrophoresis chip based on the inventive idea, electrophoresis capillaries Ch are micromachined into a body-part B of glass, e.g. pyrex-wafer, $SiO_2$ or polymer, like PMMA, PC, etc., using for example etching technology or micro-molding/hot-embossing techniques, respectively. See FIG. 2a. Into a lid part L (see FIG. 2b) electrolyte capillaries E are micromachined, which are arranged perpendicular to the electrophoresis capillaries Ch in the body part. Furthermore, there are in- and outlet openings drilled into the lid part E at the ends of the electrolyte capillaries O as well as at these positions S, which fit to the ends of the electrophoresis channels after both parts the lid L and the body B have been assembled (see FIG. 2c). The ion-conductive membrane M, necessary to separate the electrophoresis track from the electrolyte vials in form of capillaries E, e.g. a polymer membrane, is sandwiched between the body B and the lid L part by clamping, gluing or other bonding-methods (see FIG. 2d). Finally the electrophoresis channels are opened by cutting a hole into the ion-conductive membrane. The electrophoresis channels are filled with an electrophoresis-medium and the electrolyte-channels with respective electrolyte.

For operation, the chip is placed into the electrophoresis system, where electrodes (e.g. of platinum) are dipped via the electrode openings into the reservoirs with electrolyte medium. Tubes e.g. for sample injection and waste disposal are connected to in- and outlet openings of the electrophoresis chip.

To establish different electric currents and electric fields in the consecutive sections, electric currents are flowing at the joints. In order to avoid disturbances in the separation channel by electrochemical reaction products and gas-bubble formation, these electric connections are realized by inserting a solid ion conductive material as a membrane between the electrophoresis channel and each vial apart the channel. These vials are provided with electrodes and filled with appropriate electrolyte. By connecting the vial-electrodes to a direct current voltage supply, the ion interchange can take place between the vial and the channel by passing through the selective permeability material at the Joint. Thus an electric and purely ionic connection at the joint is realized.

The axial length of the Joints along channel direction are shorter (generally much shorter) than those of Sections.

A part of the non-conductive wall of the channel at the Joint is replaced by ion conductive material in order to make electric and pure ionic connection between the channel and the vial.

The shape of the electrophoretic medium inside the wall of the channel is generally a long cylinder for each Section. The shape of the interface between the ion conductor and the electrophoretic medium at the Joint should generally keep a smooth transition of the electrophoretic medium cylinders in consecutive Sections. The shape of the interface between the ion conductor and the electrophoretic medium at the Joint could be similar to a square or circular ring showing in FIG. 3a (or some parts of a ring (FIG. 3b and FIG. 3c)) around the electrophoretic medium.

Figure 2:
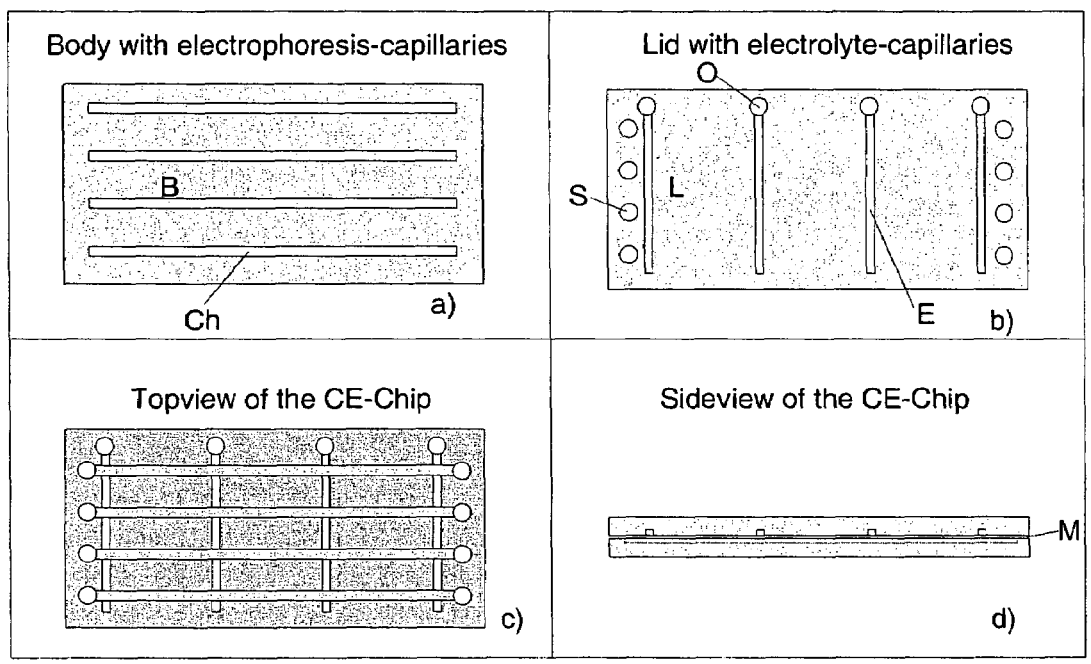
FIG. 2 a–d Part views of a miniaturized electrophoretic separating device.
Figure 3A:
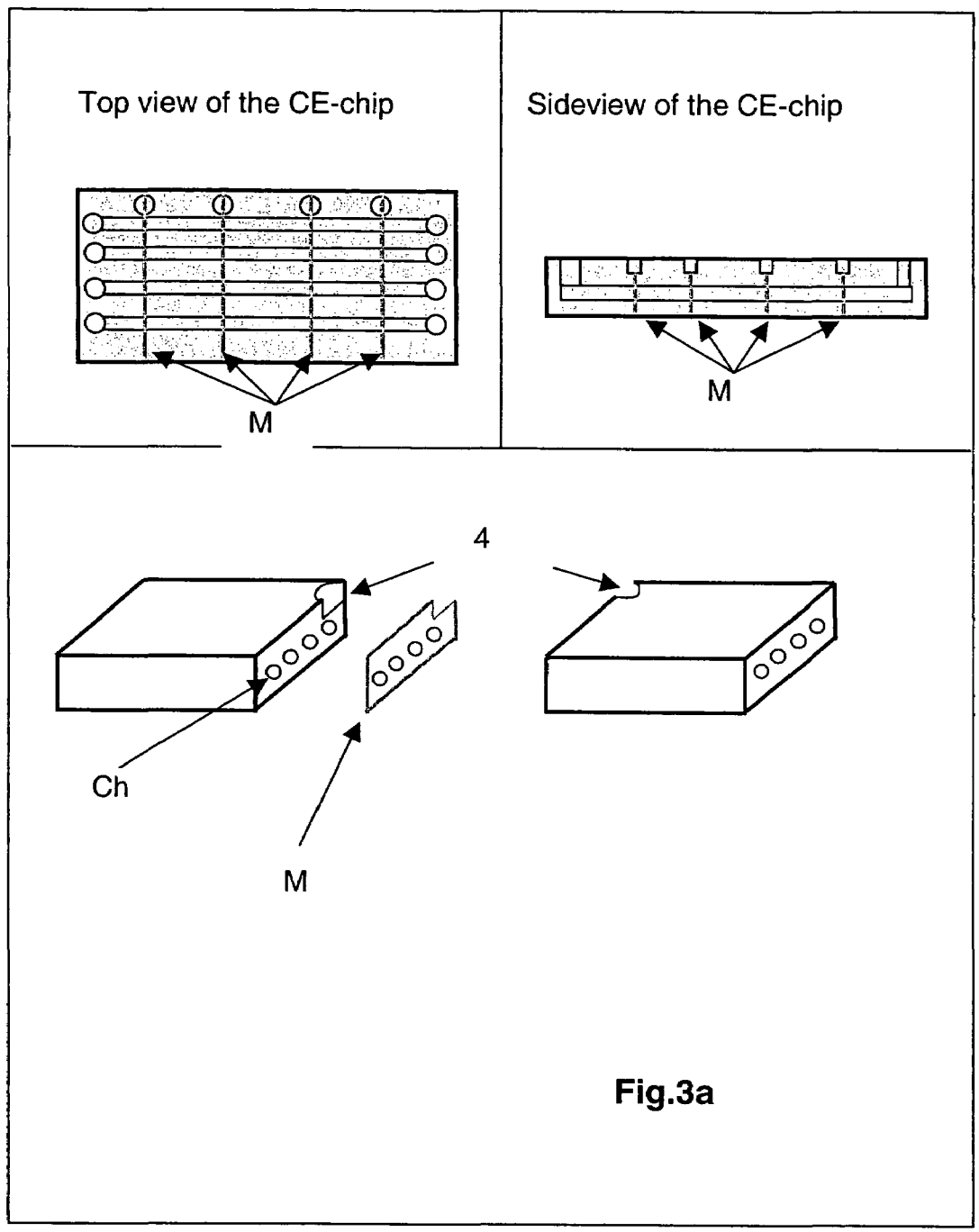
FIGS. 3a,b,c drawings showing embodiments of different joints.

The upper left sketch shows a top view, the upper right sketch a side view of a CE-Chip like it is shown in FIG. 2 but in difference of having several ion conductive membranes M traversing the electrophoresis capillaries Ch perpendicular to their extensions. A perspective view in FIG. 3a shows the way of assembly of the membrane M within said CE-Chip. At each joint $J_n$ the membrane M encircles the electrophoresis capillaries Ch completely and is connected to a vial or an electrolyte reservoir 4.

Figure 3B:
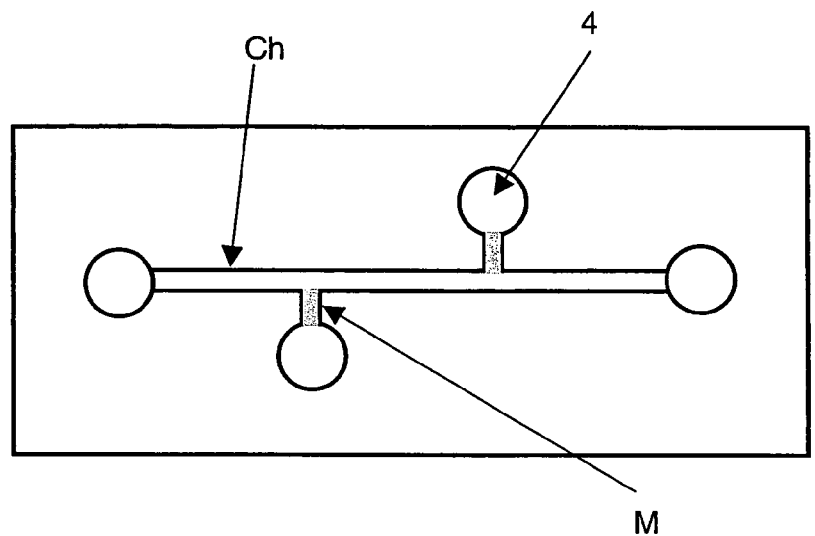
Figure 3B:
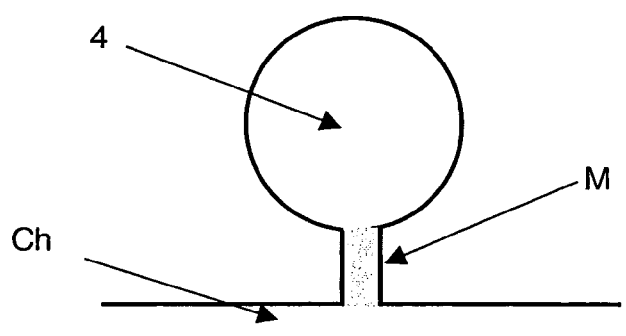
Figure 3C:
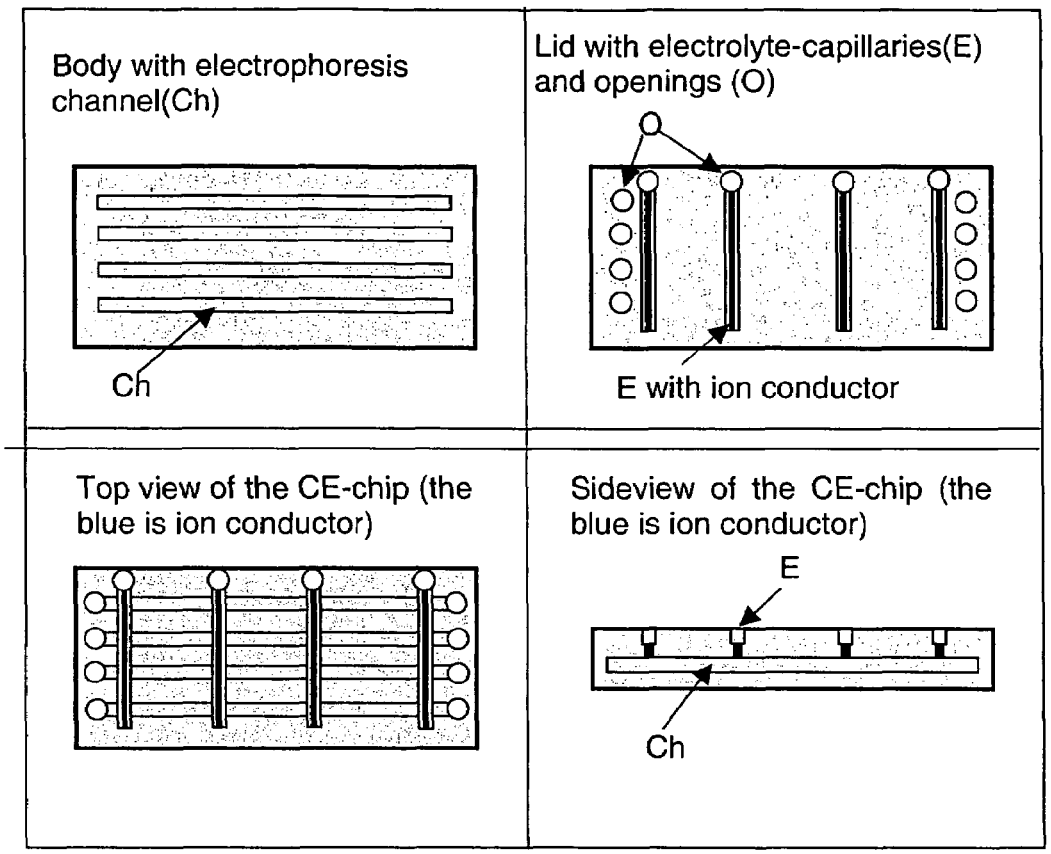
Figure 3C:
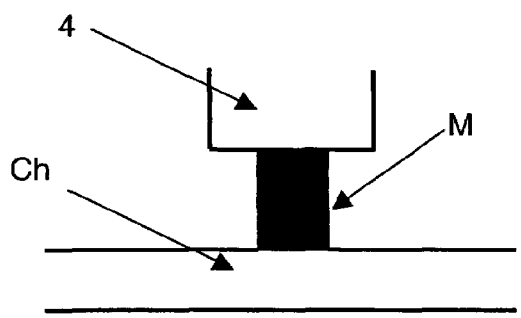

In alternative embodiments shown in FIGS. 3b and 3c the membrane M is connected to the channel Ch in kind of a part of a ring merely.

FIG. 3b shows an electrophoresis capillary Ch being connected to several electrolyte reservoirs 4 by an ion conductor M in shape of a little channel.

FIG. 3c shows in several sketches the arrangement of the connection principle shown in FIG. 3b realized on a CE-chip. The reference numbers in FIG. 3c are identical to all the before described figures.

The before described invention permits better-performance of electrophoretic demands at lower costs. The device is just right for point-of-use analytics or point-of-care diagnostics demanding cost-effective high performance capillary electrophoresis devices comprising disposable or reusable electrophoresis chips e.g. as an integral plug-in module of a generic electrophoresis system comprising fluid handling, separation, detection, data retrieval and interpretation.

Potential applications comprise serum-electrophoresis in hospital and general practitioner s laboratories to support diagnosis quickly (point-of-care) or DNA-fingerprinting for quick and reliable conviction of suspects in the field of forensic-medicine (point-of-use). Environmental and biotechnological process monitoring are other application fields of point-of-use electrophoretic analyses.

Low fabrication costs as demanded by disposable CE-chips are met by microsystems-technology in combination with alternative materials such as polymers. High separation performance of such low-cost devices is ensured by the presented novel electrophoresis method, which is distinguished through its simplicity and the usage of the special merits as provided by chip-based systems.

LIST OF REFERENCE SIGNS

1 Inlet opening
2 Outlet opening
3 Membrane, Ion conductive material
4 Reservoir, vial
5 Electrode
6 Interconnection Section
$J_n$ Joint
C Separating device
Ch Channel
L Lid
B Base
E Capillaries
M Membrane

The invention claimed is:

1. An electrophoretic separation device comprising at least one separation channel having at least one in- and outlet opening at the beginning and at the end of the at least one channel and one electrode in the region of the inlet opening and one electrode in the region of the outlet opening,
wherein said at least one separation channel is subdivided into at least two sections in series being coupled mutually by a joint providing an electrical connection means having an ion-conductive material separating said at least one channel from a reservoir being apart from the at least one channel and provided with an electrode and wherein said electrophoretic separating device is miniaturized and comprises at least a body and a lid, such that said body includes the at least one separation channel in the form of an electrophoresis capillary and the lid includes said in-and outlet openings and said reservoir.

2. The electrophoretic separating device according to claim 1,
wherein said at least one separation channel provides beside of the in- and outlet openings additional openings at the joint for inserting said ion-conductive material.

3. The electrophoretic separating device according to claim 2, wherein said ion-conductive material is a membrane.

4. The electrophoretic separating device according to claim 1,
wherein said electrodes at the in- and outlet openings as well at the joint are connectable to a voltage source in such a manner that different electric fields can be established along said respective channel sections.

5. The electrophoretic separating device according to one of the claim 1,
wherein the at least one separation channel is a capillary having a capillary diameter in the range of 0.1 µm to 1 mm and a length of 5 mm to 200 mm.

6. The electrophoretic separating device according to one of the claim 1,
wherein the at least one separation channel has channel walls coated inwardly with a polymer thin film or adsorbed film.

7. The electrophoretic separating device according to one of the claim 1,
wherein the at least one separation channel is filled or fill-able with an electrophoresis medium, being a liquid or a gel.

8. The electrophoretic separating device according to one of the claim 1,
wherein said reservoir is a vial apart the channel, provided with an electrode.

9. The electrophoretic separating device according to claim 8,
wherein said vial is filled or fill-able with an electrolyte as source for ions, which are interchangeable with ions in the electrophoresis medium channel.

10. An electrophoretic separating device, comprising:
at least one separation channel having at least one in- and outlet opening at the beginning and at the end of the at least one channel and one electrode in the region of the inlet opening and one electrode in the region of the outlet opening;
wherein said at least one separation channel is subdivided into at least two sections in series being coupled mutually by a joint providing an electrical connection means having an ion-conductive material separating said at least one channel from a reservoir being apart from the at least one channel and provided with an electrode and wherein said electrophoretic separating device is miniaturized and comprises at least a body and a lid, such that said body includes the at least one separation channel in the form of an electrophoresis capillary and the lid includes said in- and outlet openings and said reservoir;
wherein said electrodes at the in- and outlet openings as well as the joint are connectable to a voltage source in such a manner that different electric fields can be established along said respective channel sections; and
wherein said voltage source is a direct voltage source.

11. An electrophoretic separating device, comprising:
at least one separation channel having at least one in- and outlet opening at the beginning and at the end of the at least one channel and one electrode in the region of the inlet opening and one electrode in the region of the outlet opening;
wherein said at least one separation channel is subdivided into at least two sections in series being coupled mutually by a joint providing an electrical connection means having an ion-conductive material separating said at least one channel from a reservoir being apart from the at least one channel and provided with an electrode and wherein said electrophoretic separating device is miniaturized and comprises at least a body and a lid, such that said body includes the at least one separation channel in the form of an electrophoresis capillary and the lid includes said in-and outlet openings and said reservoir; and
wherein the ion conductive material is sandwiched between the lid and the body and separates the electrophoresis capillary from the reservoir.

12. An electrophoretic separating device, comprising:
at least one separation channel having at least one in- and outlet opening at the beginning and at the end of the at least one channel and one electrode in the region of the inlet opening and one electrode in the region of the outlet opening;

wherein said at least one separation channel is subdivided into at least two sections in series being coupled mutually by a joint providing an electrical connection means having an ion-conductive material separating said at least one channel from a reservoir being apart from the at least one channel and provided with an electrode and wherein said electrophoretic separating device is miniaturized and comprises at least a body and a lid, such that said body includes the at least one separation channel in the form of an electrophoresis capillary and the lid includes said in- and outlet openings and said reservoir; and wherein the body and lid as well the conductive material are arranged as a CE-Chip and are assembled by gluing, clamping, or bonding.

13. An electrophoretic separating device, comprising:

at least one separation channel having at least one in- and outlet opening at the beginning and at the end of the at least one channel and one electrode in the region of the inlet opening and one electrode in the region of the outlet opening;

wherein said at least one separation channel is subdivided into at least two sections in series being coupled mutually by a joint providing an electrical connection means having an ion-conductive material separating said at least one channel from a reservoir being apart from the at least one channel and provided with an electrode and wherein said electrophoretic separating device is miniaturized and comprises at least a body and a lid, such that said body includes the at least one separation channel in the form of an electrophoresis capillary and the lid includes said in-and outlet openings and said reservoir; and wherein said at least one first and second separation channels are arranged in parallel in an array.

14. A method for the electrophoretic separation of a sample using an electrophoretic separation device comprising at least one separation channel having at least one in- and outlet opening at the beginning and at the end of the at least one separation channel and one electrode in the region of the inlet opening and one electrode in the region of the outlet opening, wherein said at least one separation channel is subdivided into at least two sections in series being coupled mutually by a joint providing an electrical connection means having an ion-conductive material separating said at least one separation channel from a reservoir that is apart from the at least one channel and provided with an electrode, the method comprising the steps of:

injecting a sample through said inlet opening into the first section of said at least one separation channel being filled with a electrophoresis medium; and separating said sample along said at least one separation channels by applying different electrical fields in the sections to migrate the components of the sample through the at least one separation channel.

15. The method according to claim 14, wherein said sample is a complex fluid substance mixtures and occupies the complete or almost complete first section after being injected.

16. The method according to claim 14, wherein the separation is performed in one or more time periods by setting up electric fields only in the respective sections of the at least one separation channel to migrate the components of the sample from one section into the following section.

17. The method according to claim 16, wherein one period is terminated when the most slowly migrating sample component ($\mu_T$) of interest has entered the following section by passing the respective joint or when the fastest migrating component ($\mu_L$) of interest has reached the end of the following section.

18. The method according to claim 16, wherein during a first period of separation the ratio between the electric field $E_1$ in a first section and the electric field $E_2$ in a second section is a number $R_1$, not less than 1.

19. The method according to claim 18, wherein during the following periods of separation the ratio between the electric fields $E_n$ and $E_{n+1}$ in sections n and n+1 is a number $R_n$, not less than 1.

20. The method according to claim 14, wherein the separation is performed continuously.

21. The method according to claim 14, wherein electric fields $E_n$ in n consecutive sections along the at least one separation channel are set up.

22. The method according to one of the claim 14, wherein the at least one separation channel is optically recorded.

* * * * *